(12) United States Patent
Mantius

(10) Patent No.: US 9,215,885 B2
(45) Date of Patent: Dec. 22, 2015

(54) SEQUENTIAL EXTRACTION PROCESS

(75) Inventor: Harold L. Mantius, Lakeville-Middleboro, MA (US)

(73) Assignee: Ocean Spray Cranberries, Inc., Lakeville-Middleboro, MA (US)

( * ) Notice: Subject to any disclaimer, the term of this patent is extended or adjusted under 35 U.S.C. 154(b) by 435 days.

(21) Appl. No.: 12/883,961

(22) Filed: Sep. 16, 2010

(65) Prior Publication Data

US 2012/0070538 A1    Mar. 22, 2012

(51) Int. Cl.
| | | |
|---|---|---|
| *A23L 1/212* | (2006.01) | |
| *A23L 1/28* | (2006.01) | |
| *A23L 2/04* | (2006.01) | |
| *A23L 1/30* | (2006.01) | |

(52) U.S. Cl.
CPC ............ *A23L 1/212* (2013.01); *A23L 1/3002* (2013.01); *A23L 2/04* (2013.01)

(58) Field of Classification Search
USPC .......................................... 426/50, 425, 599
See application file for complete search history.

(56) References Cited

U.S. PATENT DOCUMENTS

| | | | |
|---|---|---|---|
| 4,363,264 A | 12/1982 | Lang et al. | |
| 4,497,838 A | 2/1985 | Bonnell | |
| 5,320,861 A | 6/1994 | Mantius et al. | |
| 5,419,251 A | 5/1995 | Mantius et al. | |
| 5,476,550 A * | 12/1995 | Walker | 127/2 |
| 5,646,178 A | 7/1997 | Walker et al. | |
| 5,747,088 A * | 5/1998 | Fletcher | 426/425 |
| 6,030,648 A | 2/2000 | Heldt-Hansen et al. | |
| 6,440,483 B1 | 8/2002 | Ghaedian et al. | |
| 7,022,368 B2 | 4/2006 | Mantius et al. | |
| 2005/0186324 A1 | 8/2005 | Ghaedian et al. | |
| 2009/0035432 A1 * | 2/2009 | Mantius et al. | 426/430 |
| 2012/0135109 A1 | 5/2012 | Paeschke et al. | |

FOREIGN PATENT DOCUMENTS

| | | |
|---|---|---|
| CL | 40557 | 4/2000 |
| CL | 1424-2002 | 6/2002 |

OTHER PUBLICATIONS

NPL "Countercurrent apparatus" retrieved from Handbook of food engineering practice / ed by Enrique Rotstein et al. ISBN 0-8493-8694-2, 1997 pp. 265-267, ( in Chapter 7).*
International Search Report and Written Opinion; Application No. PCT/US2010/49158; mailed Nov. 3, 2010, Applicant: Ocean Spray Cranberries, Inc.; 9 pages.
Office Action issued in U.S. Appl. No. 13/649,588 on May 8, 2014 (7 pages).
Office Action issued in U.S. Appl. No. 13/649,588 on Oct. 30, 2014 (9 pages).
Response to Office Action issued in U.S. Appl. No. 13/649,588 on May 8, 2014 filed on Aug. 19, 2014 (11 pages).
Response to Office Action issued in U.S. Appl. No. 13/649,588 on Oct. 30, 2014 filed on Jan. 30, 2015 (11 pages).
White et al., "Proximate and Polyphenolic Characterization of Cranberry Pomace," J. Agric. Food Chem. 2010. 58: 4030-4036.

* cited by examiner

*Primary Examiner* — Michele L Jacobson
*Assistant Examiner* — Bhaskar Mukhopadhyay
(74) *Attorney, Agent, or Firm* — Fish & Richardson P.C.

(57) ABSTRACT

The specification provides methods for extracting proanthocyanidins, especially from firm fruit such as cranberries, through a sequential extraction procedure, and producing infused fruit products.

22 Claims, 1 Drawing Sheet

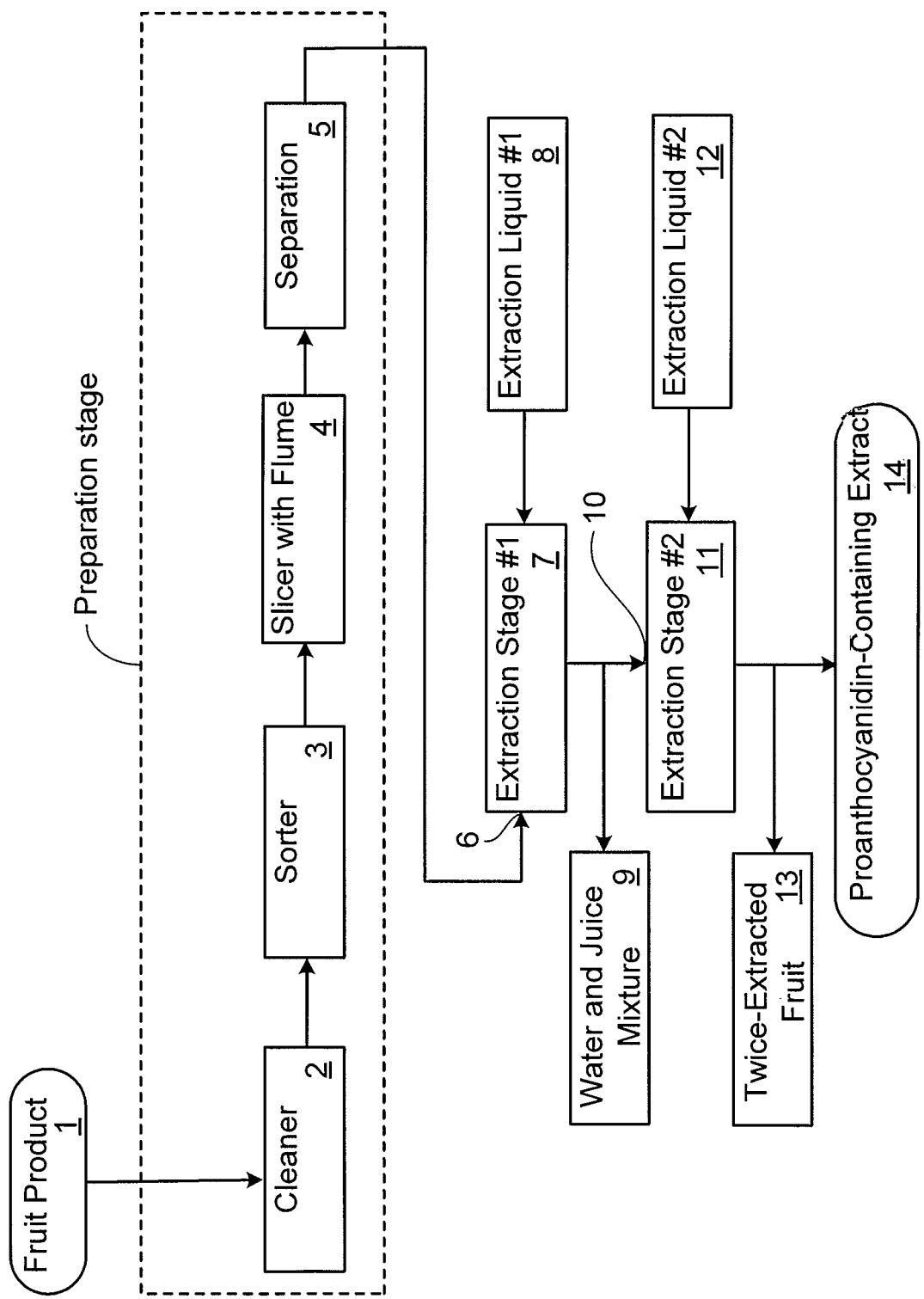

SEQUENTIAL EXTRACTION PROCESS

TECHNICAL FIELD

The claimed methods relate to the extraction of proanthocyanidins from fruits, especially cranberries, for producing various food products.

BACKGROUND

Countercurrent extractors are used in the fruit processing industry for extraction of juices from solid fruit matter. The extractor includes a screw conveyor, which advances fruit solids in a first direction while extraction fluid flows in the opposite direction, extracting juice from the solids by osmosis. See U.S. Pat. No. 5,320,861, which is incorporated herein by reference.

Certain fruits, particularly cranberries, contain a class of compounds known as proanthocyanidins (PACs; also called procyanidins, oligomeric proanthocyanidins, pycnogenols, leukocyanidins, leucoanthocyanins, and condensed tannins), which impart unique health benefits. PACs have antioxidant activity and play a role in the stabilization of collagen and maintenance of elastin—two critical proteins in connective tissue that support organs, joints, blood vessels, and muscle. Common antioxidants currently used are vitamin C and vitamin E; however, studies show that PACs' antioxidant capabilities are twenty times more powerful than vitamin C and fifty times more potent than vitamin E (Shi, J. et al., *J Med Food* 6:291-9, 2003). PACs strengthen blood vessels and improve the delivery of oxygen to cells by suppressing the production of endothelin-1 protein, which constricts blood vessels (Corder, R. et al., *Nature* 444:566, 2006). PACs also have an affinity for cell membranes, providing nutritional support to reduce capillary permeability and fragility.

The selective capture and dry weight concentration of PAC compounds may thus open up novel opportunities in the field of product application (e.g., retail beverages, lozenges) relative to delivering those unique benefits.

SUMMARY

A two-step extraction process for preparing both a juice and a proanthocyanidin-containing extract is described. In a first extraction step performed at a lower temperature, e.g., about 75° F. or less, fruit is subjected to extraction. This first extraction step removes the majority of the inherent soluble fruit component from the fruit, producing a juice. The once-extracted fruit is then subjected to a second extraction at a higher temperature, e.g., about 90° F. or more. This second extraction step removes PACs, producing a PAC-containing extract and twice-extracted fruit. One or both steps can be performed in some embodiments using a countercurrent apparatus. The two-step extraction is therefore particularly useful because PACs are removed after obtaining a high-value, high-quality fruit juice. Additionally, if pectinase enzymes are not employed in the second extraction step, the twice-extracted fruit can be used as a source of pectin, for example, to create pectin-containing products such as jellies and jams.

Accordingly, in one aspect, the present specification provides a method for processing fruit. The method includes, e.g., treating the fruit in a first extraction, wherein the first extraction is performed at a relatively low temperature, e.g., a temperature of about 75° F. or less, to thereby provide a once-extracted fruit and a juice extract; and treating the once-extracted fruit in a second extraction, wherein the second extraction is performed at a relatively high temperature, e.g., a temperature of at least about 90° F., to thereby provide a proanthocyanidin-containing extract and twice-extracted fruit.

Extractions can be performed in a number of ways. For example, in some instances, the first extraction can be performed in a countercurrent apparatus by advancing the fruit along a path while flowing an extraction liquid countercurrently to the advancing fruit, and the extraction liquid is collected to thereby provide the juice extract. In other instances, the second extraction can be performed in a countercurrent apparatus by advancing the fruit along a path while flowing an extraction liquid countercurrently to the advancing fruit, and the extraction liquid is collected to thereby provide the proanthocyanidin-containing extract. In still other instances, both the first and second extractions can be carried out in a countercurrent apparatus. That is, the first extraction can be performed in a countercurrent apparatus by advancing the fruit along a path while flowing a first extraction liquid countercurrently to the advancing fruit, and the first extraction liquid is collected to thereby provide the juice extract; and the second extraction can be performed in a countercurrent apparatus by advancing the fruit along a path while flowing a second extraction liquid countercurrently to the advancing fruit, and wherein the second extraction liquid is collected to thereby provide the proanthocyanidin-containing extract.

As another example, the first extraction can be performed in a tank, and the first extraction can include bathing the fruit in an aqueous solution. Likewise, the second extraction can be performed in a tank, and the second extraction can include bathing the once-extracted fruit in an aqueous solution. In still other instances, both the first and second extractions can be carried out in a tank. In some instances, the aqueous solution is substantially devoid of sugar and soluble fruit components.

In any of the methods described herein, the first extraction can be performed at a temperature of less than or about 70° F., e.g., at a temperature of less than or about 60° F., or less than 50° F. Further, in any of the methods described herein, the second extraction can be performed at a temperature of at least or about 100° F., e.g., at least or about 130° F., or at least or about 160° F. For example, the second extraction can be performed at a temperature of about 90° F. to about 210° F., e.g., about 100° F. to about 210° F., about 130° F. to about 210° F., or about 160° F. to about 210° F.

Further, in any of the methods, the residence time of the once-extracted fruit in the countercurrent apparatus during the second extraction can be greater than or about 30 minutes, e.g., greater than or about 60 minutes or greater than or about 90 minutes.

In any of the methods, the second extraction can extract at least 10%, e.g., at least 30%, 60%, or at least 90%, of the soluble solids that were present in the once-extracted fruit.

In some instances, the once-extracted fruit can be treated with pectinase enzymes. In other instances, extraction liquid, e.g., a first and/or second extraction liquid, is substantially free of pectinase enzymes.

In any method described herein, the fruit to be treated can be any fruit known in the art. For example, the fruit can be cranberry, blueberry, grape, cherry, blackberry, raspberry, or apple. The fruit to be treated can be a single kind of fruit or a mixture of different types of fruit.

The methods described herein can further include infusing the twice-extracted fruit with an infusion liquid to produce an infused fruit. For example, a method described herein can include treating the twice-extracted fruit with an infusion liquid in a countercurrent apparatus by advancing the fruit along a path while flowing the infusion liquid countercurrently to the advancing fruit, or in a tank. In some instances, infusion can include tumbling the twice-extracted fruit between flights of a screw conveyer by passing narrow longitudinal members positioned parallel to the axis of the screw conveyer through the twice-extracted fruit. The residence time of the fruit in the countercurrent apparatus can be any duration deemed appropriate by a skilled practitioner for infusing fruit, e.g., at least or about 10 minutes, e.g., at least or about 30 minutes, 60 minutes, or more.

In some instances, the method can include collecting infusion liquid after the infusion, concentrating the liquid, and recycling the liquid in its entirety for subsequent infusion. In some instances, about 94% to 99% of soluble solids are extracted from the twice-extracted fruit as compared to the fruit prior to treatment according to the methods.

In some instances, the infusion liquid can be formulated to have a level of inherent soluble fruit component substantially equal to or greater than the level in the twice-extracted fruit. The infusion liquid can include, e.g., fruit juice, fruit juice concentrate, corn syrup, sugar-water solution, artificial sweetener, or any combination thereof. Alternatively or in addition, the infusion liquid can include a vitamin, a flavoring (e.g., natural or artificial flavoring), a mineral, an acidulant, a colorant, or any combination thereof. The infusion liquid can comprise, e.g., about 50° to about 80° Brix, e.g., about 40° to about 60° Brix.

Infused fruit can be dried to remove water. For example, infused fruit can be dried to at least or about 76° Brix and/or to a water activity of about 0.35 to 0.62.

The infused fruit can in some instances have substantially the structural integrity of the raw fruit.

"Firm fruit" is fruit that resists structural collapse under substantial compression. Examples include, cranberries, apples, cherries, and grapes. On the other hand, "soft fruits" are more readily collapsed. Examples include blueberries, raspberries, blackberries, and the meat of various fruits especially tropical fruits, e.g., kiwi, guava, mango, and passion. "Once extracted fruit" is whole fruit or fruit piece(s) that have been subjected to extraction such that at least or about 85%, e.g., at least or about 90%, 91%, 92%, 93%, 94%, 95%, 96%, 97%, 98%, or at least or about 99%, of the inherent soluble solids have been removed. "Twice extracted fruit" is whole fruit or fruit piece(s) that have been subjected to a second extraction such that at least or about 10%, e.g., at least or about 20%, 30%, 40%, 50%, 60%, 70%, 80%, 90%, 95%, 96%, 97%, 98%, or at least or about 99%, of the residual soluble solids that were present in the once-extracted fruit feedstock have been removed. It will be understood that the processes of the claimed methods may achieve advantages such as improved yield, quality, and lower cost with many fruits. All percentages herein are by weight unless otherwise indicated or apparent.

Unless otherwise defined, all technical terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control.

Other features and advantages of the invention will be apparent from the following detailed description and FIGURE, and from the claims.

DESCRIPTION OF DRAWING

FIG. 1 depicts a flow diagram illustrating a two-step extraction procedure to extract PACs from fruit.

DETAILED DESCRIPTION

A flow diagram is shown in FIG. 1 of an exemplary two-step extraction process to extract PACs from fruit. A commercially available countercurrent apparatus can be used in the process, e.g., as described in U.S. Pat. No. 5,320,861. However, it will be understood by skilled practitioners that other types extractors and infusers may be used in the process. The process will be described for use with cranberries, although it may be adapted for use with other fruit, such as blueberries.

Countercurrent Apparatus

An exemplary countercurrent apparatus useful as an extractor includes an elongate trough-shaped housing inclined at an angle, e.g., about 2 to 6 degrees, with a helical screw conveyor intermittently rotated by a motor means, connected to a shaft on its longitudinal axis. The housing has an inlet disposed above the lower end of the screw for the introduction of the fruit to be extracted, e.g., raw cranberries, and an outlet at the higher end for the removal of extracted fruit. A charging line is provided for charging extraction liquid into the housing and a discharge line is provided for the discharge of liquid extract (e.g., a mixture of extraction liquid and soluble fruit solids). The trough temperature may be controlled using any means known to skilled practitioners, e.g., by heating with a circulating water jacket positioned about the trough. Alternatively or in addition, one may control temperature by controlling the temperature of the fruit and/or extraction liquid prior to introduction to the extractor. The screw conveyor is operated by intermittently reversing the direction of rotation of the screw. The reversal helps the relatively compacted mass of matter being extracted to be opened up enhancing the penetration of extracting liquid. Other details of a suitable countercurrent extractor and methods are described in U.S. Pat. No. 4,363,264, the entire contents of which are hereby incorporated by reference. Commercially available fruit extractor units (e.g., CCE Model 1200, Millerbernd Systems, Winsted, Minn.) may be modified and operated with beneficial results as described further below.

First Extraction

The first extraction is performed at a relatively low temperature. For example, the first extraction can be performed at a temperature of less than or about 75° F., e.g., less than or about 70° F., 65° F., 60° F., 55° F., 50° F., 45° F., 40° F., 35° F., 34° F., e.g., less than or about 33° F., but at a temperature above the point at which the extraction liquid completely freezes, or at a temperature in a range between any two of the above-referenced values. For example, the first extraction can be performed in a range of about 75° F. to about 33° F., about 70° F. to about 35° F., about 65° F. to about 40° F. or about 60° F. to about 45° F. Skilled practitioners will appreciate that any art-known method and/or apparatus can be used to perform an extraction of juice in accordance with the present invention. For example, countercurrent extraction and/or a tank system (e.g., as described in U.S. Pat. No. 6,440,483, which is incorporated by reference) can be employed in the first extraction. In an exemplary first extraction, whole raw fruit (FIG. 1, 1), which has been bulk frozen, is provided to a cleaning stage 2 to remove loose debris such as twigs, stems, leaves, soil, etc., and then conveyed to a sorting stage 3, which sorts fruit to a selected size (e.g., a minimum size specification) and removes undesirable foreign material (e.g., wood fragments and metal clips). The size-selected fruit is next passed to a slicer stage 4 (e.g., Model CC, Urschel Laboratories, Inc., Valparaiso, Ind.), which slices the berries to expose the inner pulp of the fruit unprotected by the skin, although other skin penetrating treatments such as scarifying may also be used.

The sliced fruit (e.g., at about 15° F.) can be transported, for example by means of a flume, to a separation stage 5, which can include a vibratory shaker with perforated plates, to separate the sliced fruit from the flume fluid (e.g., water; initially at about 115° F.). The thawed sliced fruit (e.g., at about 65° F.) is then provided as solid input 6 to a first extraction stage 7, which in this example employs a countercurrent apparatus (e.g., as described in U.S. Pat. Nos. 5,320,861 and 5,419,251, hereby incorporated by reference, and as described briefly above). However, it will be understood by skilled practitioners that any means of extracting juice, e.g., using other extractors known in the art, may be used in the process. Moreover, freezing of the fruit prior to processing can also be useful in that, upon rethawing, the fruit is structurally more susceptible to juice extraction. The liquid input 8 to the first extraction stage can be any suitable liquid for extracting juice, e.g., an aqueous extraction liquid (e.g., reverse osmosis permeate water without any added enzyme). The liquid output 9 of the first extraction stage is an extract mixture of extraction liquid and fruit juice. The first extraction, as discussed above, is performed at low temperature (e.g., less than 75° F.), and optionally, e.g., at a relatively high efficiency (e.g., effecting the removal of greater than 90% of the sugars and acids present in the fruit feedstock), which can avoid the detrimental effects on juice quality often associated with higher temperature extraction, such as reduced shelf-life characteristics and off notes in juice flavor stemming from elevated tannin levels. Moreover, a low temperature extraction (e.g., less than about 75° F.) preferentially removes the sugars and acids present in the fruit feedstock, leaving behind in the resultant extracted fruit a relatively higher proportion of the feedstock's inherent phytochemical content (e.g., anthocyanins and PACs). The raw juice extract from the extractor stage liquid output 9 can be further treated, e.g., as described in U.S. Pat. No. 5,320,861. Briefly, liquid output 9 can be treated, first in a separation stage to remove and collect extraneous seeds and pulp solids at a collection stage. The juice extract can also be further treated in a depectinization stage in which pectinase enzyme is provided and mixed with the juice extract. The enzyme, e.g., in amounts between about 0.01 and 0.1 percent, clears the juice extract of pectin in preparation for a filtration stage. Filtration can be achieved by means of a microfilter of, e.g., 0.1-0.5 micron pore size. The filtered juice extract can be further treated at a reverse osmosis stage where the juice extract is passed through a membrane system under pressure to semi-concentrate the juice product to about 18° Brix. This semi-concentrated juice product can then be concentrated to a higher level (e.g., about 50° Brix) through evaporative concentration as the final juice product. The cranberry juices produced by the process can have a tannin content of less than about 1900 mg/L, e.g. about 1700 mg/L (measured at 7.5° Brix).

Second Extraction

The first extraction stage 7 is followed by a second extraction stage 11 operated at a higher temperature than that of the first extraction stage (e.g., greater than or about 90° F., e.g., greater than or about 95° F., 100° F., 110° F., 112° F., 115° F., 120° F., 128° F., 130° F., 135° F., 140° F., 142° F., 143° F., 145° F., or greater than or about 150° F., 160° F., 170° F., or 180° F., or at a temperature in a range between any two of these values). For example, depending upon the desired outcome of the process, the second extraction can be performed in a range of temperatures of about 90° F. to about 190° F., e.g., about 100° F. to about 150° F., about 110° F. to about 145° F., or about 125° F. to about 145° F. Other exemplary ranges include about 138° F. to about 142° F., about 112° F. to about 118° F., about 128° F. to about 132° F., about 150° F. to about 178° F., about 178° F. to about 182° F. and about 150° F. to about 190° F. In other embodiments, the second extraction can be performed in a range of temperatures of about 90° F. to about 210° F., e.g., about 100° F. to about 210° F., about 110° F. to about 210° F., about 120° F. to about 210° F., about 130° F. to about 210° F., about 140° F. to about 210° F., about 150° F. to about 210° F., about 160° F. to about 210° F., about 170° F. to about 210° F., about 180° F. to about 210° F., about 190° F. to about 210° F., about 200° F. to about 210° F., or about 205° F. to about 210° F. Skilled practitioners will appreciate that any art-known method and/or apparatus can be used to perform this second extraction in accordance with the present invention. For example, countercurrent extraction and/or a tank system (e.g., as described in U.S. Pat. No. 6,440,483, which is incorporated by reference) can be employed. In an exemplary second extraction stage, the once-extracted fruit from stage 7 is provided as solid input 10 to a second extraction stage 11, which in this example employs a countercurrent apparatus, e.g., an extractor as described above and in U.S. Pat. Nos. 5,320,861 and 5,419,251. The extractor used in the second extraction may be, e.g., the same extractor used in the first extraction or a second, different extractor. When a different extractor is used for the second extraction, the once-extracted fruit may be moved, e.g., via a vibratory conveyor from the first extractor to the second extractor. The extraction temperature may be controlled using any means known to those of skill in the art, e.g., by regulating the trough temperature (e.g., by heating with a circulating water jacket positioned about the trough). Alternatively or in addition, one may control temperature by controlling the temperature of the fruit and/or extraction liquid prior to introduction to the extractor.

The liquid input 12 to the extractor can be any liquid suitable for extracting PACs, e.g., an aqueous extraction liquid, e.g., reverse osmosis permeate water with or without any added enzyme. Moreover, enzymes, e.g., pectinase enzymes, can be added to increase the yield of PACs extracted from the fruit during the second extraction stage. Pectinase for use in the present methods can be obtained from any source, and is commercially available from, e.g., DSM Food Specialties USA, Inc., and Novozymes Switzerland AG. The residence time of the fruit in the extractor during the second extraction can be, e.g., about 90 to about 150 minutes, e.g., about 100 to about 140 minutes, about 110 to about 130 minutes, or about 120 to about 125 minutes. In some instances, the residence time can be at least or about 30 minutes, e.g., at least or about 60 minutes. Further, skilled practitioners will appreciate that the residence time of the fruit in the extractor can be adjusted upwardly or downwardly (e.g., to less than 60 minutes, e.g., about 10 minutes to about 60 minutes) based on the desired outcome and any number of factors and conditions. The solid output of the extraction stage 11 is a twice-extracted fruit 13. The liquid output 14 of the extraction stage 11 is a PAC-containing extract.

Twice-extracted fruit, e.g., exiting as solid output 13 of extraction stage 11, is typically characterized by the removal of at least or about 10%, e.g., at least or about 20%, 30%, 40%, 50%, 60%, 70%, 80%, 90%, 95%, 96%, 97%, 98%, or at least or about 99%, of the residual soluble solids that were present in the once-extracted fruit feedstock.

Infusion

Twice-extracted fruit may be processed, e.g., as described in U.S. Pat. No. 5,320,861, hereby incorporated by reference, to produce an infused fruit, though it will be understood by skilled practitioners that other infusers and methods may be used in the process. Twice-extracted fruit lacking, to a greater degree than once-extracted fruit, the inherent color of the fruit feedstock may be useful for producing uniquely colored infused fruit products, e.g., products with colors different than the original fruit. In an exemplary method, the twice-extracted fruit 13 is provided to an infusion stage, which can employ a countercurrent apparatus that may be as described above and in U.S. Pat. No. 5,320,861. Skilled practitioners will appreciate that a countercurrent extractor can also function as an infuser. The infuser can be, e.g., the same apparatus as that used in the first and/or second extraction stage, or a different infuser.

In an exemplary infusion method, the twice-extracted fruit is supplied to an infusion stage, including a countercurrent apparatus similar to that used at extraction stages 7 or 11, as discussed with respect to FIG. 1. Liquid input at the infusion stage is any infusion liquid, e.g., sugar-water (e.g., fructose) solution, high fructose corn syrup, grape juice, strawberry juice, raspberry juice, blueberry juice, apple juice, or any combination thereof, or concentrates thereof. An infusion liquid may include a natural flavoring (e.g., cinnamon), an artificial flavoring (e.g., artificial sweetener), a vitamin (e.g. ascorbic acid), a mineral (e.g. iron), an acidulant (e.g., citric acid), and/or a colorant (e.g., elderberry concentrate). The infusion liquid may have any soluble solids level as measured in ° Brix, e.g., about 68° Brix, and can be provided from a continuous process loop that blends infusion liquid from the liquid output of the infusion stage with fresh infusion syrup from a fresh infusion liquid supply to produce an infusion syrup blend. Excess infusion liquid from the liquid output of the infusion stage can be treated in a vibratory screen separation apparatus (e.g., Model X548, Sweco, Inc., Florence, Ky.) to remove and collect extraneous seeds and pulp solids at a collection stage. The excess infusion liquid from the liquid output of the infusion stage can be concentrated at a concentration stage. Finally, the excess infusion liquid from the liquid output of the infusion stage can be treated at a blend stage, which may include input from a fresh infusion liquid supply, before being recycled to the liquid input of the infuser as a component of the resulting infusion syrup blend. As discussed above, any infusion liquid can be formulated to include a desired amount of natural or inherent soluble fruit component, equal to or greater than the amount present in the twice-extracted fruit so that no net extraction of inherent soluble fruit component into the infusion media occurs during infusion.

The infused fruit product exiting the infusion stage as the solid output can be passed to a screening stage. At the screening stage, the infused fruit product can be separated from excess infusion liquid coating the solid product and collected at a collection stage, while the excess infusion liquid can be screened to remove extraneous insoluble solids (e.g., seeds and pulp), re-concentrated, blended with fresh infusion syrup from a fresh infusion liquid supply, and recycled to the liquid input of the infuser as a component of the resulting infusion syrup blend. The infused fruit product can be provided to a dryer stage. Drying temperature and conditions can be, e.g., in the range of about 150° F. to 240° F. for about 120 minutes using a conventional forced air fruit dryer. The final infused dried fruit product can next be passed to an oiler stage, which includes an oil supply, wherein vegetable oil or the like is applied to the fruit product to reduce product stickiness and enhance appearance. The final infused dried product can be collected at a collection stage from which it may be bulk packaged. The dried product can have, e.g., a soluble solid content corresponding to about 76° Brix up to about 88° Brix. The flavor of the fruit product, moreover, is imparted, at least in part, by the infusion liquid, which may be of many varieties including a controlled amount of flavor of the original fruit. A coating may be applied that also contributes to flavor and/or nutrient value.

EXAMPLES

The invention is further described in the following examples, which do not limit the scope of the invention described in the claims.

A two-step extraction procedure to extract PACs from cranberries was performed as described above. Bulk-frozen cranberries were subjected to a standard first extraction at low temperature (e.g., less than about 75° F.) to provide a juice extract and once-extracted fruit. Second extractions were performed on the once-extracted fruit to extract PACs. Four different sets of second extraction conditions were tested, each set being tested in one second extraction or "run." Each of the four runs differed mainly in extraction temperature and the use of pectinase enzymes. The four runs can be generally described as follows:

A. Extractor Temperature: 115° F.; no enzyme added;
B. Extractor Temperature: 128° F.; no enzyme added;
C. Extractor Temperature: 142-144° F.; no enzyme added; and
D. Extractor Temperature: 113-114° F.; pectinase enzyme added.

As shown in Table 1, a greater yield of PACs was obtained with second extractions performed at elevated temperatures. In this regard, 25% of PACs were extracted in Run A, which was performed at 115° F. The yield of PACs increased to 34% when the extraction was performed at 128° F. (Run B). The yield increased an additional two-fold to 66% when the extraction was performed at 142-144° F. (Run C).

As can been seen in Table 1, Run D, extraction efficiency can also be increased by the addition of pectinase enzymes. These enzymes catalyze the hydrolysis of pectin, a polysaccharide that is found in the cell walls of plants. The conditions of Run D are similar to those of Run A except that in Run D, pectinase enzyme was also added. As a result of the added enzyme, Run D was more than twice as efficient as Run A in extracting PACs from once-extracted cranberries.

These examples clearly demonstrate that extraction efficiency is a function of temperature and pectinase enzymes. It will be understood by skilled practitioners that higher PAC yields could be obtained by manipulating process conditions, e.g., employing higher extraction temperatures and/or different enzyme systems.

TABLE 1

Four Separate Extractions Performed on Once-Extracted Cranberries (Hulls)

| Run | A | B | C | D |
|---|---|---|---|---|
| Hull Feedrate (g/min.) | 225 | 225 | 225 | 450 |
| Hull PACs (%, dwb) | 6.76 | 6.03 | 6.25 | 6.66 |
| Hull Solids (%) | 3.88 | 4.91 | 3.66 | 4.14 |
| Extraction Water Feedrate (g/min.) | 900 | 900 | 900 | 450 |
| Extractor Residence Time (min.) | 121 | 121 | 120 | 120 |
| Extractor Temperature (° F.) | 115 | 128 | 142-144 | 113-114 |
| Pectinase Enzyme Usage (g/min.) | 0 | 0 | 0 | 0.1 |
| Extracted Hull Discharge (g/min.) | 204.1 | 226.8 | 159.2 | ND |
| Extracted Hull PACs (%, dwb) | 3.48 | 3.59 | 1.72 | ND |
| Extracted Hull Solids (%) | 5.32 | 5.17 | 5.24 | ND |
| Liquid Extract Discharge (g/min) | 926.5 | 889.3 | 975.1 | 684.4 |

TABLE 1-continued

Four Separate Extractions Performed on Once-Extracted Cranberries (Hulls)

| Run | A | B | C | D |
|---|---|---|---|---|
| Liquid Extract PACs (%, dwb) | 22.84 | 25.19 | 10.21 | 6.17 |
| Liquid Extract Soluble Solids (° Brix) | 0.07 | 0.1 | 0.34 | 1.65 |
| Material Balance Error (g/min.) | 5.6 | 8.9 | 9.3 | ND |
| Material Balance Error (%) | 0.50 | 0.79 | 0.83 | ND |
| PAC Input (g/min.) | 0.59 | 0.67 | 0.52 | 1.24 |
| PAC Output (g/min.) | 0.53 | 0.64 | 0.48 | 0.70 |
| PAC Material Balance Error (%) | 10.93 | 3.15 | 6.47 | ND |
| PAC Yield (%) Recovered in Liquid Extract | 25.08 | 33.65 | 65.70 | 56.18 |

ND: not determined

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for processing proanthocyanidin-containing fruit, the method comprising:
treating the proanthocyanidin-containing fruit in a first extraction by advancing the fruit along a path while flowing a first extraction liquid countercurrently to the advancing fruit, wherein the first extraction is performed at a temperature of about 75° F. or less, to thereby provide a once-extracted fruit and a juice extract; and
treating the once-extracted fruit in a second extraction by advancing the fruit along a path while flowing a second extraction liquid countercurrently to the advancing fruit, wherein the second extraction is performed at a temperature of at least about 100° F. for at least 30 minutes, to thereby provide a proanthocyanidin-containing extract and twice-extracted fruit.

2. A method for processing proanthocyanidin-containing fruit, the method comprising:
treating the proanthocyanidin-containing fruit in a first extraction in a tank by bathing the fruit in a first extraction liquid, wherein the first extraction is performed at a temperature of about 75° F. or less;
collecting the first extraction liquid to thereby provide a juice extract and once-extracted fruit;
treating the once-extracted fruit in a second extraction in a tank by bathing the fruit in a second extraction liquid, wherein the second extraction is performed at a temperature of at least about 100° F. for at least 30 minutes; and
collecting the second extraction liquid to thereby provide a proanthocyanidin-containing extract and twice-extracted fruit.

3. The method of claim 1, wherein the first extraction, the second extraction, or both, is performed in a countercurrent apparatus.

4. The method of claim 1, wherein the first extraction is performed at a temperature of less than 70° F.

5. The method of claim 1, wherein the second extraction is performed at a temperature of at least about 115° F.

6. The method of claim 1, wherein the second extraction is performed at a temperature of about 110° F. to about 210° F.

7. The method of claim 1, wherein the second extraction extracts at least 10% of the soluble solids that were present in the once-extracted fruit.

8. The method of claim 1, further comprising treating the once-extracted fruit with pectinase enzymes.

9. The method of claim 1, wherein the first extraction liquid is free of added pectinase enzymes.

10. The method of claim 1, wherein the second extraction liquid is free of added pectinase enzymes.

11. The method of claim 1, wherein the fruit is a proanthocyanidin-containing cranberry.

12. The method of claim 1, further comprising infusing the twice-extracted fruit with an infusion liquid to thereby produce an infused fruit.

13. The method of claim 12, wherein infusing comprises treating the twice-extracted fruit with the infusion liquid by advancing the fruit along a path while flowing the infusion liquid countercurrently to the advancing fruit.

14. The method of claim 13, wherein infusing is performed in a countercurrent apparatus.

15. The method of claim 12, wherein infusing is performed in a tank.

16. The method of claim 12, further comprising formulating the infusion liquid to have a level of inherent soluble fruit component equal to or greater than the level in the twice-extracted fruit.

17. The method of claim 12, wherein about 94 to 99% of soluble solids have been extracted from the twice-extracted fruit as compared to the fruit prior to processing.

18. The method of claim 12, wherein the infusion liquid is about 50° to about 80° Brix.

19. The method of claim 12, wherein the fruit is infused to about 40° to 60° Brix.

20. The method of claim 12, further comprising drying the infused fruit to remove water.

21. The method of claim 12, further comprising drying the infused fruit to at least about 76° Brix.

22. The method of claim 1, wherein the second extraction is performed for about 90 minutes to about 150 minutes.

* * * * *